(12) United States Patent
Hagele

(10) Patent No.: US 7,846,140 B2
(45) Date of Patent: Dec. 7, 2010

(54) MINI EYE DROP TIP

(76) Inventor: James Hagele, 13262 Evergreen Dr., Nevada City, CA (US) 95959

( * ) Notice: Subject to any disclaimer, the term of this patent is extended or adjusted under 35 U.S.C. 154(b) by 1307 days.

(21) Appl. No.: 11/001,254

(22) Filed: Nov. 30, 2004

(65) Prior Publication Data

US 2006/0116649 A1    Jun. 1, 2006

(51) Int. Cl.
*A61M 35/00* (2006.01)
(52) U.S. Cl. ............ 604/295; 604/298
(58) Field of Classification Search ........ 604/294–302
See application file for complete search history.

(56) References Cited

U.S. PATENT DOCUMENTS

| | | | |
|---|---|---|---|
| 1,900,201 A | 3/1933 | Sager | |
| 2,728,491 A | 12/1955 | Aneshansley | |
| 2,783,919 A | 3/1957 | Ansell | |
| 3,261,355 A | 7/1966 | Burbig | |
| 3,756,478 A | 9/1973 | Podell | |
| 4,173,226 A | 11/1979 | Shell | |
| 4,338,936 A | 7/1982 | Nelson | |
| 4,605,398 A | 8/1986 | Herrick | |
| 4,792,334 A | 12/1988 | Py | |
| 4,917,274 A | 4/1990 | Asa | |
| 4,927,062 A | 5/1990 | Walsh | |
| 4,946,452 A | 8/1990 | Py | |
| 5,007,905 A | 4/1991 | Bauer | |
| 5,030,214 A | 7/1991 | Spector | |
| 5,069,675 A | 12/1991 | Menchel | |
| 5,127,553 A | 7/1992 | Weinstein | |
| 5,133,702 A * | 7/1992 | Py | ............................. 604/302 |
| 5,163,929 A * | 11/1992 | Py | ............................. 604/298 |
| 5,267,986 A | 12/1993 | Py | |
| 5,387,202 A | 2/1995 | Baron | |
| 5,611,788 A | 3/1997 | Marchment | |
| 5,624,057 A * | 4/1997 | Lifshey | ...................... 222/212 |
| 5,833,675 A | 11/1998 | Garcia | |
| 5,848,999 A * | 12/1998 | Basilice et al. | ............... 604/300 |
| 6,041,978 A | 3/2000 | Hagele | |
| 6,129,248 A | 10/2000 | Hagele | |
| 6,135,985 A | 10/2000 | Fromer | |
| 6,197,008 B1 | 3/2001 | Hagele | |
| 6,632,202 B1 | 10/2003 | Hagele | |
| 6,736,802 B1 * | 5/2004 | Recanati | ...................... 604/295 |
| 2005/0043693 A1 | 2/2005 | Infantolino | |
| 2005/0049562 A1 | 3/2005 | Cress | |

* cited by examiner

*Primary Examiner*—Patricia M Bianco
*Assistant Examiner*—Lynne Anderson
(74) *Attorney, Agent, or Firm*—Heisler & Associates

(57) ABSTRACT

A tip is provided for a liquid dropper which facilitates formation of a mini drop, a mini drop being a drop smaller than a standard typical drop. A conduit is provided extending from a reservoir of liquid to a tip. The tip provides a location for release of the mini drop. The tip includes a rim surrounding a port with the rim having a particularly thin wall and with the port being particularly narrow. The dimensions of the rim and port facilitate formation of the mini drop. The material forming the tip is flexible and resilient so that should the tip come into contact with sensitive structures, such as an eye of a patient, a potential for injury is minimized. Dispensers featuring the unique tip are disclosed in multiple different embodiments for attachment to a bottle of liquid to be dispensed, or to fit over an existing outlet.

33 Claims, 3 Drawing Sheets

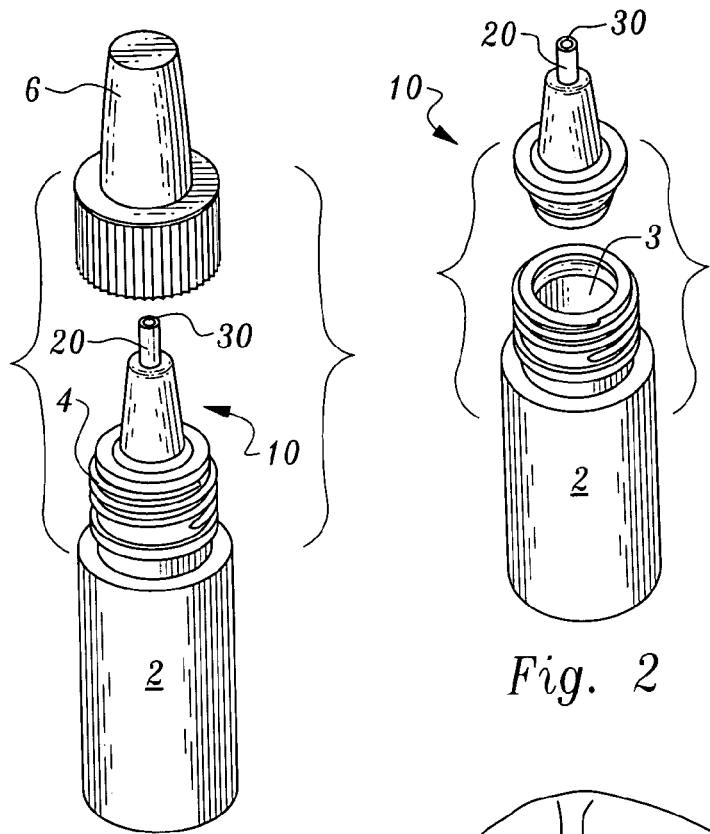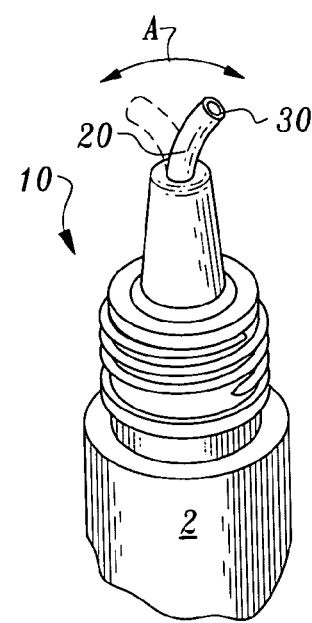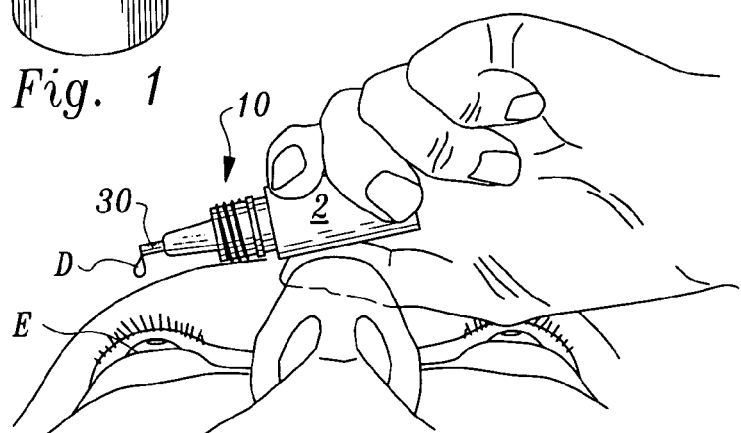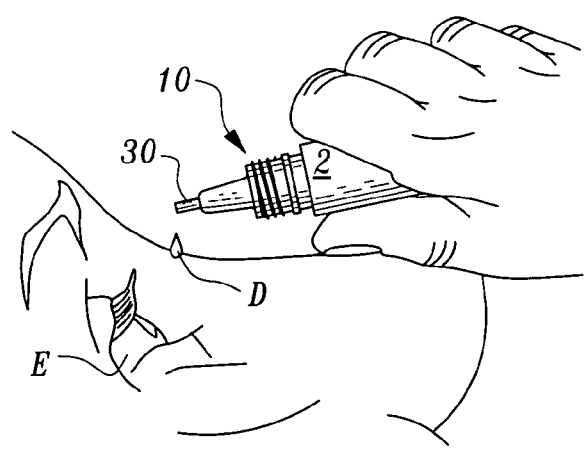
Fig. 1
Fig. 2
Fig. 4
Fig. 3
Fig. 5

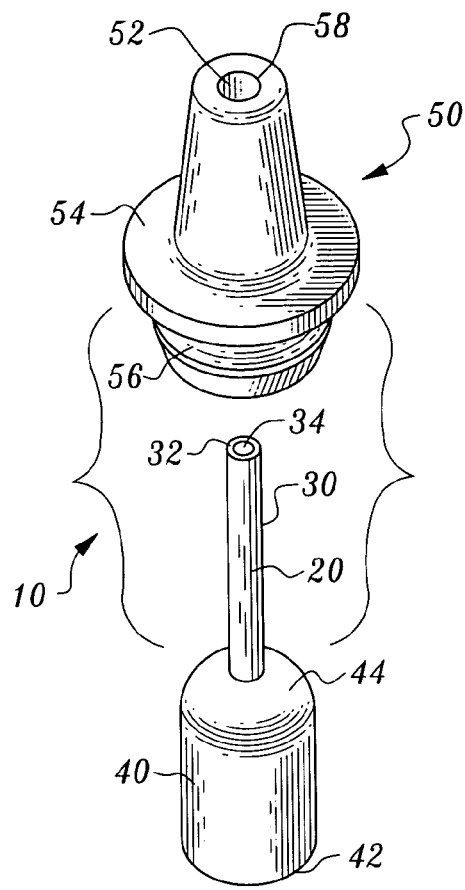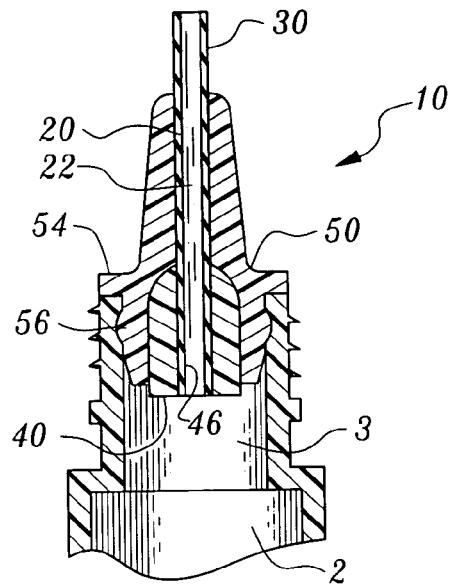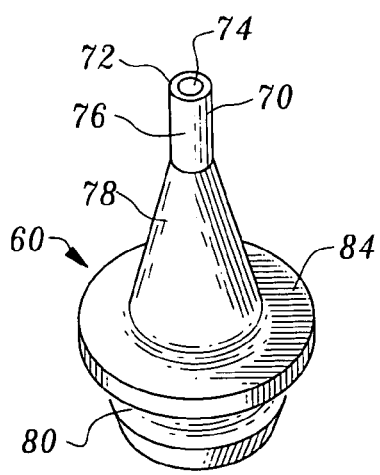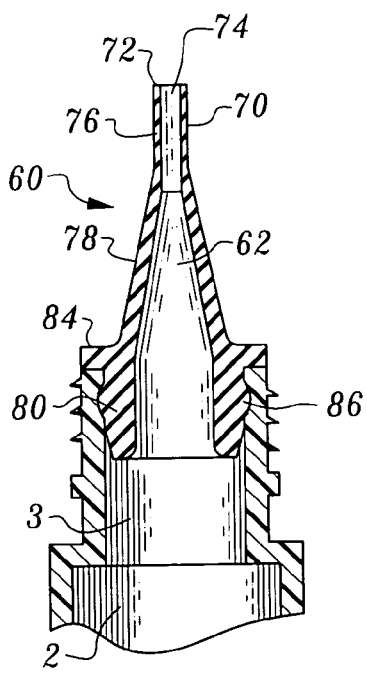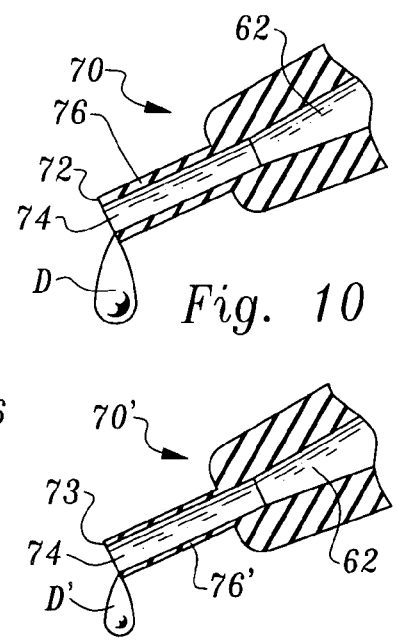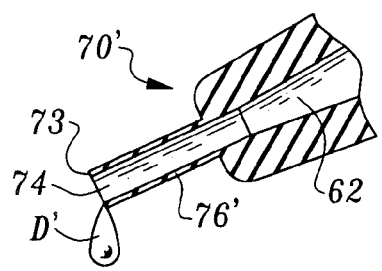

MINI EYE DROP TIP

FIELD OF THE INVENTION

This invention relates to eye dropper tips for the dispensing of medicinal liquids into the eye. More particularly, this invention relates to eye dropper tips that create much smaller drops than current conventional eye dropper tips.

BACKGROUND OF THE INVENTION

The placement of medicinal liquid into a patient's eye tends not only to be difficult but wasteful. The eye dropper bottles and tips on the market today produce a large drop and often more than one drop spontaneously falls from the dropper bottle either into the eye or onto the skin of the face and eyelids. This not only creates a waste of drops, but can be irritating to the skin and eye.

This invention creates a small droplet that falls from the free end of the tip rather than migrating along the outer surface of the stem of the dropper. The accumulation of liquid along the outer stem surface of a conventional dropper tip, when held in a near horizontal orientation, will tend to produce a larger and larger drop as liquid is expressed from the reservoir until the force of gravity overcomes the surface tension and causes the drop to fall. The drop created by the tip according to the method of this invention is much smaller and more consistent in size, falls freely from the distal end of the tip and is more easily instilled into the eye.

The creation of a very small drop is important in the treatment of various ocular conditions, but it is especially important in the treatment of Keratitis Sicca or "dry eye." Millions of people suffer from some type of tear dysfunction. Many individuals do not make an adequate amount of tears and thus the eye may have symptoms of burning, irritation or sandy feeling, itching, and even a decrease in visual acuity since the tear film is responsible for maintaining good vision.

The normal tear film over the eye consists of three layers: an outer lipid or oily layer, a middle aqueous or watery layer and an inner layer of mucin that holds the rest of the tear film to the cornea and outer structures of the eye. The tear volume in a normal healthy eye is estimated to be about six microliters, a microliter being $\frac{1}{1,000,000}$th of a liter. The size of a drop from a conventional eye dropper on the market today ranges from approximately fifty to sixty microliters, some eight or more times the normal volume of tear in the eye. A mini drop instilled into an eye that is only twelve microliters (some two times the tear volume) would provide much more benefit to the eye compared to the flushing and washing action of too much liquid. Since the drop produced is very small, it would greatly reduce the need for the use of tissues to dry excess liquid from the eyelids and skin. This would spare the lipids that are necessary along the eyelid margins.

Presently there are dozens of artificial tears on the market that can be purchased over the counter. Most of them not only produce a large drop for the eye, but the directions on the bottle suggest that more than one drop may be used. This sudden excess of moisture that is instilled into the eye at one time may be more harmful than beneficial if it irrigates away the mucin, lipid layer and proteins of the tear film. Also, when an excess of medicinal drop is used, the patient wipes the eye profusely with tissue or cloth and thereby risks the removal of the beneficial lipids that are produced by the oil glands of the eyelids.

If artificial tears are instilled into an eye too frequently, there is the fear of washing out the more beneficial components of the tear film, such as the mucin layer, the lipid layer and other elements. Most artificial tears are designed to replace the aqueous or watery portion of the tear film. Thus, if a very small droplet is created for instillation, a person may use drops more frequently and still preserve the beneficial components of the tear film that the eye naturally produces. More frequent and smaller drops may help repair the dehydrated cells of the cornea and conjunctiva, along with providing more comfort to the eye. If a smaller droplet is used in the eye, the patient will have much less need for wiping off the excess medication from the eye and eyelids and thus preserve the lipid that is secreted by the oil glands that open onto the marginal surface of the eyelids. The repeated use of tissues for removing the excess medication from the eye and eyelids may be dehydrating and counter productive to the treatment of the dry eye.

It can be shown that when a regular size drop from a conventional eye dropper is instilled into the eye, an excess of liquid flows onto the eyelashes and skin of the face. This liquid dries and can be observed under the biomicroscope to produce numerous flakes of dried liquid that are formed and adhere to the skin of the face and eyelids. These dried flakes of medication on the skin of the eyelids can form up to one-half inch away from the lower eyelid margin. When the dry eye is treated with eye drops four or five times a day, one can readily see the problem of irritation to the skin and eyelids from these dried particles.

Contact lens wearers often have symptoms of dryness of the eyes, especially when the lenses are worn for longer periods of time or in certain situations where dehydration of the eye occurs. Medicated drops and artificial tears have been designed to help alleviate the symptoms that come from these conditions and may be instilled as needed. When a large drop or drops are instilled into an eye with a patient wearing contact lenses, there is a tendency for this large volume to "float" the lens and can cause it to slide off the cornea where it must remain for good visual acuity. However, when a mini drop is instilled into an eye with a contact lens, the small amount of liquid is beneficial for the relieving of the symptoms and yet much less likely to cause the lens to move out of its proper place. Also, since the volume is very small, drops may be used more often and without the problems that come from excessive moisture.

There are numerous other applications for the use of a very small drop in various eye conditions and diseases. One example is that certain anti-glaucoma medications have the side effect of causing eyelashes to grow and thicken. If a smaller amount of drop is instilled into an eye, there will be much less chance of coating the eyelashes and the eyelids and thus reducing this side effect. Also, less medication on the eyelids reduces the irritation and allergy that is often seen with medications that are frequently used in the eyes.

A smaller drop is more desirable when using various drops for testing purposes. An example is when a person is being tested for glaucoma. Applanation tonometry is the most common method used to test for intraocular pressure. It is necessary to use a drop containing sodium fluorscein and a topical anesthetic to do this test. The conventional bottles that contain these ingredients for testing purposes will form a drop that is three to four times the volume of the mini drop produced by the present invention. This volume from the mini drop tip, even though much smaller, is still adequate to perform the test easily and successfully. The advantages are two-fold. First, much less drop is used and therefore a savings in cost is provided. However, the greater advantage is that the patient is not left with an excess of yellow dye in the eye and on the eyelids when the test is completed. Patients are much happier without this side effect as they leave the examining room. By using a smaller amount of dye when testing for glaucoma, abnormal stain patterns may be seen with the biomicroscope that would otherwise be covered up with the large amount of fluid in the eye that comes from conventional dropper tips.

Most standard eye droppers are described in the prior art as somewhat conically-shaped with a larger base end of the tip attached to a reservoir of liquid eye medication. The free end of the tip is penetrated by an opening through which each drop of liquid eye medication is discharged. With the distal end of a standard tip directed downward, an eye drop will likely fall from the opening in the tip toward a point on the patient's eye directly below the opening of the tip.

As the tip is rotated from an inverted position toward a more horizontal position, liquid flowing out the opening of the standard tip will have a tendency to spread over and wettably adhere to a portion of the exterior surface of the tip. Once the exterior surface of the tip becomes wetted by the liquid medication, each drop of liquid exiting the opening in the tip will flow along the wetted surface to accumulate at a point adjacent the boundary between the wetted and dry portion of the tip. As the discharged liquid flows to this boundary, sufficient mass will accumulate until a drop falls from a point adjacent the boundary. Consequently, the drop no longer falls from the end of the tip. Although a patient may have the end of the prior tip located directly above the eye, the drop will likely roll down the tip to release at a point away from the end of the tip and miss the eye altogether.

Accordingly, a need exists to make a dropper tip for eye drops or other mini drops that consistently creates a small droplet that falls freely from the distal portion of the tip rather than adhering to the outer surface of the stem of the tip. Such a dropper tip should be made of a soft, supple material rather than a rigid material in order to reduce any harm that might come from an accidental touching of the external structures of the eye.

SUMMARY OF THE INVENTION

The present invention is an improved tip for droppers, such as for eye drops, to dispense and instill medicinal liquids into a patient's eye. The dropper creates a much smaller drop of liquid than conventional dropper tips and is thus beneficial in treating such conditions as the dry eye. It is designed so that the droplet falls from the distal free end of the tip rather than adhering and traveling along the outer surface of the stem of the tip even when held in a near horizontal orientation over the eye. The tip has a unique shape and is made of a soft, supple material. The tip of the present invention is integrated with a reservoir of medicinal liquid. The reservoir is squeezed to dispense medicinal liquid out the small opening in the distal free end of the tip. The diameter of the external opening of the tip is extremely small and the walls of the external opening of the tip are very narrow. This combination provides for the creation of a small droplet that consistently falls from the distal free end of the tip rather than adhering to the external surface of the tip. The present invention dropper tip fits into any conventional eye dropper bottle.

This invention permits the bottle to be held either at a near vertical position or at a near horizontal orientation and still give more accuracy in delivering the drop to the intended target. The present invention provides for creating a small droplet to instill into the eye and permits the dropper bottle to be held either vertically or horizontally over the eye.

Eye dropper tips are not to touch the eye during normal use because of possible harm to ocular structures and also risk of contamination. However, unintentional contact can occur. The distal end of the dropper tip of the present invention is made of a soft and supple material, thus reducing the harm that might come from an accidental touching of the eye. The external opening of the tip is extremely small in diameter and the walls of the opening of the tip are very narrow, thus providing little area for a drop to be held to the tip by surface tension. This provides for the falling of the drop from the free end of the dropper tip as a small droplet.

OBJECTS OF THE INVENTION

Accordingly, a primary object of the present invention is to provide a tip for a dropper, such as an eye dropper, which consistently creates a smaller droplet than conventional dropper tips now available.

Another object of the present invention is to provide a tip for an eye dropper which causes the drop to fall from the distal free end of the tip when the eye dropper bottle is held in either a vertical or a horizontal position over the eye.

Another object of the present invention is to make a tip that has an extremely small external opening for the drop to be emitted from the walls of that external opening are very narrow in order to reduce the surface area for drop adherence to the outer tip surface.

Another object of the present invention is to provide a tip made of a soft, supple material to reduce any harm to the eye if a person accidentally touches the outer structures of the eye.

Another object of the present invention is to provide a tip for an eye dropper which allows a patient to keep his or her head in a more upright position during application to avoid potential dizziness and vertigo.

Another object of the present invention is to provide a dropper tip that, when held more horizontally, does not require the elevation of the shoulder or the marked internal rotation of the wrist to instill a drop into the eye.

Another object of the present invention is to provide a tip for an eye dropper which is of simple and reliable manufacture.

Other further objects of the present invention will become apparent from a careful reading of the included drawing figures, the claims and detailed description of the invention.

BRIEF DESCRIPTION OF THE DRAWINGS

FIG. 1 is a perspective view of a bottle, such as an eye drop bottle with the dispenser of a first embodiment attached to the bottle, and with a cap for covering the dispenser and connecting to the bottle.

FIG. 2 is a perspective view similar to that which is shown in FIG. 1 but with the cap removed and with the dispenser shown exploded away from the bottle.

FIG. 3 is a bottom plan view of the dispenser of FIG. 1 in use by a patient to instill an eye drop from the bottle through the dispenser.

FIG. 4 is a detail of a portion of that which is shown in FIG. 1, illustrating how the tip of the dispenser is capable of flexing.

FIG. 5 is a side elevation view similar to that which is shown in FIG. 3 and illustrating use of the dispenser to dispense an eye drop from a bottle.

FIG. 6 is an exploded parts view of the dispenser alone and illustrating the two part construction of the dispenser of the first embodiment.

FIG. 7 is an assembled full sectional view of that which is shown in FIG. 6.

FIG. 8 is a perspective view of a second embodiment dispenser which is provided with unitary construction from a single mass of material.

FIG. 9 is a full sectional view of the dispenser of FIG. 8 and attached to a bottle.

FIG. 10 is a sectional view of a detail of a dispenser generally similar to the unitary dispenser of FIGS. 8 and 9, and illustrating how a relatively large diameter port and relatively thick cylindrical sides produce a relatively large drop.

FIG. 11 is a full sectional detail view similar to that which is shown in FIG. 10 but with a tip having thinner sides and illustrating how a smaller drop is provided.

DESCRIPTION OF THE PREFERRED EMBODIMENTS

Figure 12:
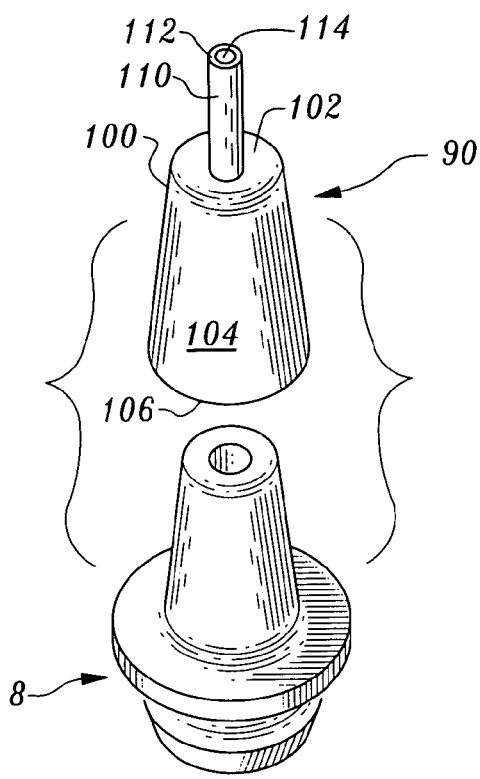
FIG. 12 is a perspective view of a cover dispenser adapted to be attached to a standard outlet of a bottle to retrofit the benefits of the dispensers of this invention onto a standard dropper bottle.
Figure 13:
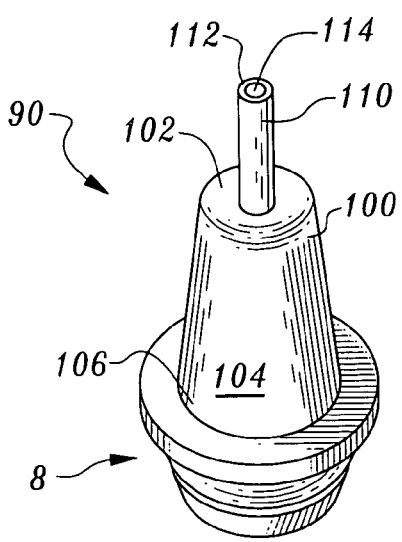
FIG. 13 is a perspective view of the cover dispenser of FIG. 12 with the cover dispenser fully in position upon the standard outlet of the bottle.

Referring to the drawings, wherein like reference numerals represent like parts throughout the various drawing figures, three illustrative embodiments of this invention are particularly described. These embodiments are described in detail to illustrate the invention as expressed in particular embodiments. However, these embodiments are not provided to limit the scope of this invention. A dispenser 10 (FIGS. 1-7) is provided according to a first embodiment. This dispenser 10 is attachable to a bottle 2, such as an eye drop containing dropper bottle so that the dispenser 10 provides an outlet for eye drops from the bottle 2. The dispenser 10 particularly provides for safe and precise release of mini drops from the dispenser, mini drops being any drops smaller than a standard drop.

In essence, and with particular reference to FIGS. 1-7, basic details of the dispenser 10 of the first embodiment are described. The dispenser 10 provides a conduit 20 extending from a source of the liquid drops to a distal tip 30 where the drops D are released. Most preferably, this dispenser 10 is formed of two separate structures connected together. These two separate structures include a base 40 to which the conduit 20 and distal tip 30 are secured, and a collar 50 into which the base 40 and conduit 20 are received.

A second embodiment (FIGS. 8-11) is provided in the form of a unitary dispenser 60. The unitary dispenser 60 is distinct from the dispenser 10 of the first embodiment in that the unitary dispenser 60 is provided as a single unitary mass of material, rather than two separate structures connected together. The unitary dispenser 60 has a free tip 70 from which the drops D are released. A coupling end 80 is provided which allows the unitary dispenser 60 to be coupled to the bottle 2, so that a reservoir of liquid within the bottle 2 can feed the unitary dispenser 60.

A cover dispenser 90 (FIGS. 12-17) provides a third illustrated embodiment of this invention. The cover dispenser 90 is configured to attach to a bottle 2 which already has a standard outlet coupled thereto. Thus, with the cover dispenser 90, a combined bottle 2 with a standard outlet 8 can be fitted with the cover dispenser 90, converting the bottle 2 with the standard outlet 8 into a bottle 2 configured to take advantage of the unique attributes of the dispenser 10 of the first embodiment, namely delivery of a mini drop of consistently small size in a safe fashion and at a precise location. The cover dispenser 90 includes a cone 100 with a hollow interior adapted to overlie the outlet 8. An apex tip 110 extends from the cone 100 and delivers the drops D (FIGS. 10 and 11) from the cover dispenser 90. Various attachment structures are utilized to secure the cover dispenser 90 to the standard outlet 8.

More specifically, and with particular reference to FIGS. 1 and 2, details of the bottle 2 to which the dispenser 10 of the first embodiment is attached, are described. The bottle 2 is preferably a hollow generally cylindrical enclosure with flexible side walls surrounding an interior reservoir. An opening 3 (FIG. 2) is provided at an upper end of the bottle 2 from which liquid can enter and exit the reservoir within the bottle 2. Typically, threads 4 surround the opening 3 and facilitate attachment of a cap 6 with complemental threads to the opening 3 of the bottle 2. In the first embodiment, any standard outlet 8 (FIGS. 12-17) has been removed so that the opening 3 is left without any structure closing the opening 3. The opening 3 is thus available to receive the dispenser 10 of the first embodiment within the opening 3. The dispenser 10 can be utilized with various different bottles 2 of different sizes and shapes.

With particular reference to FIGS. 2, 4, 6 and 7, particular details of the dispenser 10 of the first embodiment are described. The dispenser 10 provides a structure which can be coupled to the opening 3 of the bottle 2 and from which drops D (FIGS. 3 and 5) can be released. The dispenser 10 includes the conduit 20 generally passing entirely through the dispenser 10 from an uppermost portion of the dispenser 10 at the distal tip 30, to a lowermost portion of the dispenser 10 at the base 40. This conduit 20 includes a central bore 22 (FIG. 7) passing along an entire length thereof, so that liquids can pass through the conduit 20.

The conduit 20 is preferably formed of a flexible resilient material, such as rubber. One material which is particularly useful is a material such as that which is utilized to form surgical tubing. For instance, silicone tubing, such as that provided by the Storz Instrument company of St. Louis, Mo. The material is preferably sufficiently flexible to flex over 90° from an original center line, but will perform to some degree if at least 30° of flexing is facilitated. The material is preferably sufficiently rigid to avoid flexing significantly when only experiencing gravity loads.

The conduit 20 is uniquely particularly sized to produce mini drops. A mini drop is generally described as any drop which is smaller than a standard drop. A standard drop typically has a volume of between fifty and sixty microliters. Factors which determine the size of a drop include surface tension characteristics of the liquid, characteristics of the material from which the drop is released, and the geometry of the conduit 20 from which the drop is released. In particular, the interior diameter of the conduit 20 and the wall thickness of the conduit 20 affect drop D size. With the inner diameter reduced, drop D size is reduced. With wall thickness reduced, drop D size is reduced.

With the dispenser 10 drop D size is controlled primarily by controlling the inner diameter and the wall thickness of the distal tip 30 at the upper end of the conduit 20. In particular, the distal tip 30 includes a rim 32 (FIG. 6) defining an uppermost portion of the conduit 20. A port 34 defines the hole surrounded by the rim 32. By making the rim 32 sufficiently thin and the port 34 sufficiently small in diameter, a small drop D, referred to as a "mini drop" is provided. In particular, by restricting the thickness of the rim 32 to approximately half a millimeter and by keeping the port 34 width to one millimeter, a mini drop having a volume of between fifteen and twenty microliters can consistently be provided. For a smaller mini drop, smaller rim 32 and/or port 34 dimensions can be used. If slightly larger mini drops are desired, the rim 32 and/or port 34 dimensions can be increased.

Experimentation has shown that when the distal tip 30 is configured as described above, drops D of remarkably consistent small size are produced. Furthermore, the drops D have a strong tendency to hang from the distal tip 30 rather than rolling back away from the distal tip 30. The drop D is believed to remain in place at the distal tip 30 because of the small wall thickness of the rim 32, and also because of characteristics of the rubber material forming the conduit 20.

The dispenser 10 can be held nearly horizontal (see FIGS. 3 and 5) and still have the drop D drop from the distal tip 30 for precise installation into the eye, or otherwise precisely delivering the drops D to a location where desired. These dimensional features of the distal tip 30 are generally repeated in each of the embodiments disclosed herein, while other aspects of the various dispensers of these three embodiments are modified to facilitate secondary factors such as ease of manufacture and ease of installation to a bottle 2.

With the dispenser 10, the entire dispenser 10 is preferably formed from two separate structures including the base 40 and the collar 50 (FIG. 6). The base 40 has the conduit 20 fixed thereto (FIGS. 6 and 7). The base 40 includes a flat side 42 at a bottom most surface and a domed side 44 at an uppermost surface. A bore 46 passes vertically down through the base 40 which is sized to receive the conduit 20 therein. The conduit 20 is preferably bonded to the base 40 within the bore 46. Alternatively, the conduit 20 could be formed with the base 40.

The collar 50 provides a structure which fits into the opening 3 of the bottle 2, and which receives the base 40 and associated conduit 20 therein. The collar 50 includes a central throat 52 sized to receive the conduit 20 passing therethrough. The conduit 20 is allowed to extend entirely through the central throat 52 and provide lateral support for the conduit 20, while allowing the conduit 20 to extend beyond a brim 58 at an uppermost portion of the collar 50.

A flange 54 defines a widest portion of an exterior of the collar 50, which is preferably substantially circular and acts as a stop when the collar 50 is placed into an opening 3 of a bottle 2. A rib 56 preferably extends radially beneath the flange 54 and snaps into a corresponding depression in the opening 3 of the bottle 2, to snap the collar 50 securely into the opening 3 of the bottle 2. The collar 50 preferably has an interior lower portion which is generally domed and with a contour similar to that of the base 40, so that the base 40 can be securely received within the collar 50.

Typically, the base 40 and collar 50 would both be formed from injection molded plastic materials. Thus, the base 40 and collar 50 are preferably more rigid than the conduit 20. Preferably, the conduit 20 is bonded to the base 40, but not to the collar 50.

The resilient nature of the material forming the conduit 20 allows the conduit 20 to flex laterally, such as along arrow A of FIG. 4. Also, because the conduit 20 is not bonded to the collar 50 within the central throat 52, the conduit 20 is capable of collapsing axially somewhat into the central throat 52 of the collar 50.

While it is not desirable to let eye drop dispensers, such as the dispenser 10, contact the surface of the eye E in any way, such accidental contact can occur unintentionally. It is desirable to form the distal tip 30 of the conduit 20 from a material which facilitates flexing (arrow A of FIG. 4) and potentially axial collapsing somewhat, such that should the distal tip 30 contact the eye E, the potential for damage to the eye E is minimized. Furthermore, because production of mini drops according to this invention requires a particularly thin rim 32 wall thickness and particularly small overall width dimensions of the distal tip 30, the potential for this tip 30 to scratch or otherwise damage the eye E would be increased if not for the flexible resilient nature of the material forming the distal tip 30.

Materials of various compositions and hardnesses could be used for the conduit 20 and tip 30, with the material facilitating bending of the tip 30 when light touching of the tip to a sensitive structure such as an eye occurs. The material is preferably sufficiently hard that it does not flex noticeably when not loaded and held horizontally (FIGS. 3 and 5).

With particular reference to FIGS. 8-11, details of the second embodiment unitary dispenser 60 are described. The unitary dispenser 60 is generally similar to the dispenser 10 of the first embodiment except that the unitary dispenser 60 is formed from a single unitary mass of material. The unitary dispenser 60 includes a central opening 62 which acts as a pathway for liquid to travel from the bottle 2 interior reservoir up to the free tip 70. The free tip 70 includes a rim 72 surrounding a port 74. Cylindrical sides 76 are provided generally analogous to the walls of the conduit 20 described in detail with regard to the dispenser 10 of the first embodiment. These cylindrical sides 76 preferably transition into tapering sides 78 joining the free tip 70 to the coupling end 80 of the unitary dispenser 60. The coupling end 80 includes a flange 84 and rib 86 analogous to those described above with respect to the collar 50 of the dispenser 10 of the first embodiment. Thus, the coupling end 80 utilizes the flange 84 and rib 86 to securely connect the unitary dispenser 60 to the opening 3 of the bottle 2.

The material forming the unitary dispenser 60 could be homogeneous or include different components exhibiting differing hardnesses and flexibility properties. Most preferably in this embodiment, the unitary dispenser 60 is formed entirely of a rubber or soft flexible plastic material similar to that provided for the conduit 20 of the dispenser 10.

FIG. 10 illustrates in detail how the drop D hangs from the rim 72 of the free tip 70. The drawing shown in FIG. 10 is slightly different from that shown in FIGS. 8 and 9, but generally analogous to the unitary dispenser 60 of FIGS. 8 and 9. In FIG. 11, a thin rim 73 is substituted for the rim 72 of FIG. 10. A smaller drop D' results, with the smaller drop D' shown suspended from the thin rim 73 at the free tip 70 supported by the cylindrical side 76' which is thinner than the cylindrical side 76 of FIG. 10. While FIG. 11 illustrates the production of a mini drop D' by making the rim 73 thinner than the rim 72 of FIG. 10, a similar result can be achieved by making an inner diameter of the port 74 smaller. By experimentation with various rim wall thicknesses and port 74 diameters, appropriate combinations can be determined which allow for repeatable mini drops to be produced having a desired volume. As with the conduit 20 and distal tip 30 of the dispenser 10 of the first embodiment, at least the free tip 70 of the unitary dispenser 60 is preferably formed of a flexible and resilient material for the benefits described in detail above.

With particular reference to FIGS. 12-17, details of a cover dispenser 90 are described. The cover dispenser 90 is configured to attach over a bottle 2 which already has a standard outlet 8 coupled thereto, and without requiring removal of the standard outlet 8. In particular, the cover dispenser 90 provides a cone 100 with a hollow interior. The cone 100 has a crest 102 at an uppermost portion thereof extending down along tapering sides 104 to a foot 106. The taper of the tapering sides 104 is preferably provided to be generally similar to a taper in the standard outlet 8 which is typically already attached to the bottle 2 through the opening 3.

Figure 14:
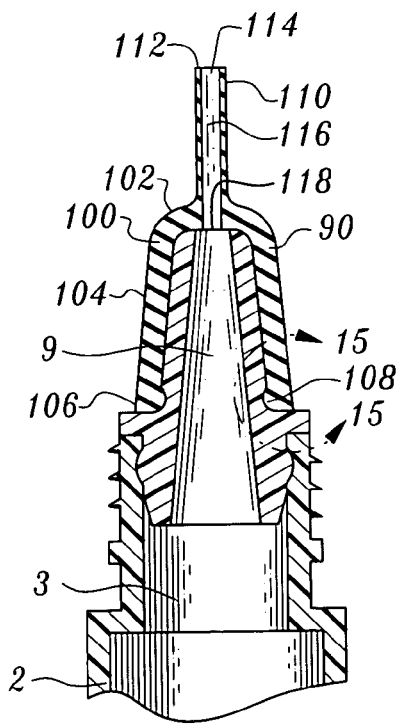
FIG. 14 is a full sectional view of that which is shown in FIG. 13 in a first attachment embodiment utilizing a bump and notch combination.
Figure 15:
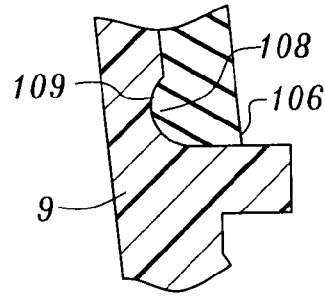
FIG. 15 is a detail of a portion of that which is shown in FIG. 14.

In one embodiment shown in FIGS. 14 and 15, a bump 108 is provided extending radially inwardly from the foot 106. The standard outlet 8 is in the form of an outlet with notch 9 with the notch sized to receive the bump 108 so that the cover dispenser 90 snaps onto the outlet with notch 9 by having a bump 108 snap into the notch 109.

An apex tip 110 is provided which extends up from the crest 102 of the cone 100. The apex tip 110 has an uppermost portion defined by a rim 112, surrounding a port 114. A cylindrical bore 116 extends through the apex tip 110 with the cylindrical bore 116 extending from the port 114 down to an entrance 118 which passes into an interior of the cone 100 generally adjacent where liquid is allowed to pass from the standard outlet 8 or outlet with notch 9. The apex tip 110 is generally analogous to the free tip 70 and distal tip 30 of previous embodiments and is thus formed of a flexible and resilient material. The cone 100 can either be formed of the same material forming the apex tip 110 or can be formed of a more rigid material or a material having other desirable properties.

Figure 16:
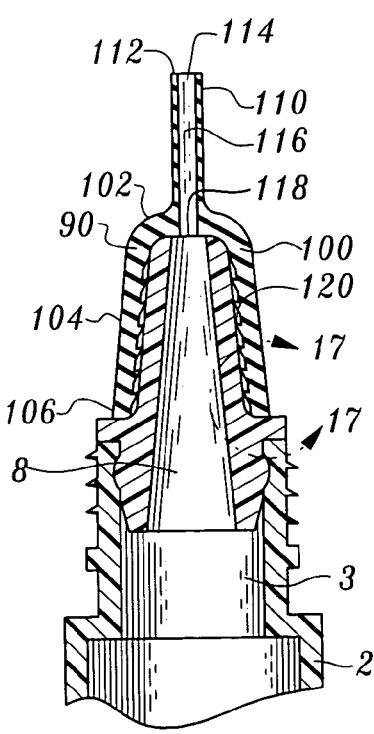
FIG. 16 is a full sectional view of that which is shown in FIG. 13 and illustrating a toothed attachment embodiment for the cover dispenser of FIG. 13.
Figure 17:
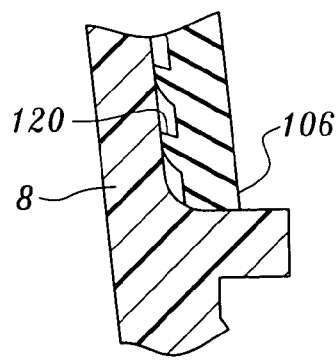
FIG. 17 is a detail of a portion of that which is shown in FIG. 16.

In the embodiment of FIGS. 16 and 17, the bump 108 and notch 109 of FIGS. 14 and 15 are replaced with teeth 120 extending from the tapering sides 104 of the cone 100 in an inward direction. These teeth 120 are serrated and have a biased angle which tends to cause the teeth 120 to dig into the standard outlet 8 to secure the cover dispenser 90 upon the standard outlet 8, without requiring any modification to the standard outlet 8.

The bump 108 and notch 109 combination (FIGS. 14 and 15) or the teeth 120 (FIGS. 16 and 17) provide two forms of a means to secure the cover dispenser 90 to the outlet of a bottle containing the liquid to be dispensed. Other securing means could include use of an adhesive, fasteners, various different arrangements of complemental bumps and recesses, threads, or other structures or attachment methodologies. Once the cover dispenser 90 is secured over the outlet of the bottle 2, the cover dispenser 90 can be used in a similar fashion to the dispenser 10 and unitary dispenser 60 of previous embodiments.

This disclosure is provided to reveal a preferred embodiment of the invention and a best mode for practicing the invention. Having thus described the invention in this way, it should be apparent that various different modifications can be made to the preferred embodiment without departing from the scope and spirit of this invention disclosure. When structures are identified as a means to perform a function, the identification is intended to include all structures which can perform the function specified. When structures of this invention are identified as being coupled together, such language should be interpreted broadly to include the structures being coupled directly together or coupled together through intervening structures. Such coupling could be permanent or temporary and either in a rigid fashion or in a fashion which allows pivoting, sliding or other relative motion while still providing some form of attachment, unless specifically restricted.

What is claimed is:

1. An eye drop dispenser, comprising in combination:
   an elongate conduit having an inlet at a first end thereof and an outlet at a second end thereof;
   said inlet coupled to a source of liquid eye drop material;
   said outlet located at a tip of said conduit;
   said tip formed of a supple material; and
   wherein said tip exhibits a thin wall with a thickness of up to about half a millimeter.

2. The dispenser of claim 1 wherein a width of said tip is sufficiently small to release a mini eye drop having a volume less than that of a typical size eye drop.

3. The dispenser of claim 2 wherein a width of said tip is sufficiently small to produce a mini eye drop having a volume up to half of a typical eye drop.

4. The dispenser of claim 2 wherein said tip is substantially circular in cross-section with an outer diameter sufficiently small to cause drops dispensed from said tip to have a volume of less than twenty-five microliters.

5. The dispenser of claim 1 wherein said tip is formed of a resilient material tending to return to an original position when no forces are applied to said tip.

6. The dispenser of claim 5 wherein said tip is sufficiently supple to facilitate flexing at least 90° away from a centerline aligned with an original position for said tip.

7. The dispenser of claim 6 wherein said tip is formed of material having sufficient firmness to avoid substantial flexing of said tip when said tip is held horizontally and is loaded only with gravity loads, and being sufficiently supple to flex easily when contacting a sensitive structure such as an external eye.

8. The dispenser of claim 1 wherein said source of liquid includes a reservoir inside a bottle, with said conduit coupled to a collar, said collar adapted to be attached to the bottle.

9. The dispenser of claim 8 wherein said collar is adapted to be press fit into an opening in the bottle.

10. The dispenser of claim 9 wherein said collar is sized to fit within the opening of the bottle.

11. The dispenser of claim 9 wherein said collar is adapted to fit over a rigid dropper bottle tip coupled to the opening in the bottle.

12. The dispenser of claim 11 wherein said collar includes a cone with a hollow interior sized to accommodate the rigid dropper bottle tip and a bump thereon sized to snap into a circumferential notch in the standard rigid tip so that the collar can snap onto the standard rigid tip with said tip coupled to said collar.

13. The dispenser of claim 11 wherein said collar includes a cone with a hollow interior sized to accommodate the rigid dropper bottle tip and with teeth on an interior surface of said cone adapted to engage portions of the standard rigid tip to hold said collar and said tip upon said collar in position relative to the bottle.

14. The dispenser of claim 1 wherein said source of liquid includes a reservoir inside a bottle having flexible walls.

15. A method for instilling a small drop into an eye, including the steps of:
   providing a dispenser having an elongate conduit with an inlet at a first end thereof and an outlet at a second end thereof, said inlet coupled to a source of liquid eye drop material, said outlet located at a tip of said conduit, said tip formed of a supple material, wherein a width of said tip is sufficiently small to produce a mini eye drop having a volume less than that of a typical eye drop;
   causing a drop of liquid to form on the tip;
   bringing the tip near the eye;
   transferring the drop to the eye by the drop falling freely from the tip into the eye; and
   easily flexing the tip for protection should the tip accidentally contact the eye by first forming the tip of a sufficiently supple material to allow flexing at least 90° away from a centerline aligned with an original position of said tip.

16. The method of claim 15 wherein said transferring step includes the step of allowing the drop on the tip to freely fall onto an inside surface of a lower eyelid adjacent the eye.

17. The method of claim 15 wherein said transferring step includes the step of orienting the tip extending non-vertically from the source of liquid eye drop material.

18. The method of claim 17 wherein said transferring step includes the step of orienting the tip closer to horizontal than to vertical relative to the source of eye drop material.

19. The method of claim 15 including the further step of sizing the tip sufficiently small to produce a mini eye drop having a volume up to half of that of a typical eye drop.

20. The method of claim 19 wherein said sizing step further includes the step of configuring the tip to exhibit a thin wall with a width of up to about half a millimeter.

21. The method of claim 15 including the further steps of:
   locating the source of liquid eye drop material within a reservoir inside a bottle with flexible walls; and
   squeezing the bottle to initiate said causing step.

22. A dispenser for drops of liquid, the dispenser comprising in combination:
   a liquid reservoir with a central axis aligned with a centerline of said reservoir;
   a conduit extending substantially along said centerline from said liquid reservoir to a tip;
   said tip having a port therein for discharging the liquid; and
   said tip formed of a supple material.

23. The dispenser of claim 22 wherein said tip is formed of a resilient material tending to return to an original position when no forces are applied to said tip.

24. The dispenser of claim 23 wherein a width of said tip is sufficiently small to produce a mini drop having a volume less than that of a typical drop.

25. The dispenser of claim 23 wherein said tip is substantially circular in cross-section with an outer diameter sufficiently small to cause drops dispensed from said tip to have a volume of less than twenty-five microliters.

26. The dispenser of claim 24 wherein said tip exhibits a thin wall with a width of up to about half a millimeter.

27. A dispenser cover for a liquid dropper, the liquid dropper having an outlet coupled to a liquid source, the dispenser cover comprising in combination:
   a cover adapted to be attached to the outlet of the dropper;
   a tip affixed to said cover, said tip having a port therein;
   a bore extending within said tip from an entrance to said port; said entrance adapted to be in fluid communication with the outlet of the dropper when said cover is attached to the dropper;
   wherein said tip is formed of a supple material; and
   wherein said tip is sufficiently supple to facilitate flexing at least 90° away from a centerline aligned with an original position for said tip before flexing.

28. The dispenser cover of claim 27 wherein said tip is formed of a resilient material tending to return to an original position when no forces are applied to said tip.

29. The dispenser cover of claim 27 wherein said tip is formed of a material having sufficient firmness to avoid substantially flexing when held horizontally and experiencing gravity loads, and sufficiently supple to flex when impacting sensitive structures, such as an eye.

30. The dispenser cover of claim 27 wherein a width of said tip is sufficiently small to produce a mini drop having a volume less than that of a typical eye drop.

31. The dispenser cover of claim 30 wherein said tip is sufficiently small to produce a mini drop having a volume of up to half of a typical drop.

32. The dispenser cover of claim 27 wherein said tip is substantially circular in cross-section with an outer diameter sufficiently small to cause drops dispensed from said tip to have a volume of less than twenty-five microliters.

33. The dispenser cover of claim 27 wherein said tip exhibits a thin wall with a width of up to about half a millimeter.

* * * * *